US005475137A

United States Patent [19]

Shimada et al.

[11] Patent Number: 5,475,137

[45] Date of Patent: Dec. 12, 1995

[54] M-PHENYLENEDIAMINE DERIVATIVES

[75] Inventors: Tomoyuki Shimada; Masaomi Sasaki; Tamotsu Aruga; Hiroshi Adachi, all of Shizuoka, Japan

[73] Assignee: Ricoh Company, Ltd., Tokyo, Japan

[21] Appl. No.: 224,440

[22] Filed: Apr. 7, 1994

Related U.S. Application Data

[62] Division of Ser. No. 939,619, Sep. 2, 1992, Pat. No. 5,334,470.

[30] Foreign Application Priority Data

| | | | |
|---|---|---|---|
| Sep. 2, 1991 | [JP] | Japan | 3-248363 |
| Sep. 2, 1991 | [JP] | Japan | 3-248364 |
| Sep. 25, 1991 | [JP] | Japan | 3-273418 |
| Nov. 21, 1991 | [JP] | Japan | 3-332476 |
| Dec. 9, 1991 | [JP] | Japan | 3-350314 |

[51] Int. Cl.$^6$ .......... C07C 211/61

[52] U.S. Cl. .......... 564/308; 564/426

[58] Field of Search .......... 564/308, 426

[56] References Cited

U.S. PATENT DOCUMENTS 5,001,569 10/1991 VanSlyke et al. .......... 428/457

FOREIGN PATENT DOCUMENTS 4-036264 2/1992 Japan .
4-117349 4/1992 Japan .

*Primary Examiner*—Richard L. Raymond
*Attorney, Agent, or Firm*—Oblon, Spivak, McClelland, Maier & Neustadt

[57] ABSTRACT

An electrophotographic photoconductor is composed of an electroconductive substrate and a photoconductive layer formed thereon including a m-phenylenediamine derivative of formula (I):

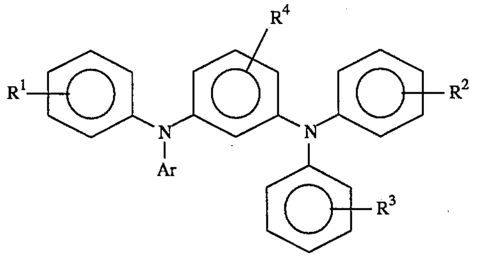

(I)

wherein Ar represents a non-condensed polycyclic hydrocarbon group other than a phenyl group, or a condensed polycyclic hydrocarbon group having not more than 18 carbon atoms; and $R^1$, $R^2$, $R^3$ and $R^4$ each represent hydrogen, a halogen atom, a cyano group, a nitro group, an alkyl group, an alkoxyl group, an aryl group, an aryloxy group, an alkylmercapto group, a group represented by

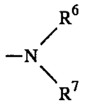

in which $R^6$ and $R^7$ each represent hydrogen, an alkyl group, or an aryl group, an alkylenedioxy group or an alkylenedithio group. Novel m-phenylenediamine derivatives for use in the electrophotoconductor and intermediates for producing the m-phenylenediamine derivatives, and methods of those derivatives are disclosed.

12 Claims, 4 Drawing Sheets

M-PHENYLENEDIAMINE DERIVATIVES this is a division of application Ser. No. 07/939,619, filed on Sep. 2, 1992, now U.S. Pat. No. 5,334,470.

BACKGROUND OF THE INVENTION

1. Field of the Invention

The present invention relates to an electrophotographic photoconductor comprising an electroconductive substrate and a photoconductive layer formed thereon comprising at least one m-phenylenediamine derivative or N-Phenyl-N-(3-aminophenyl)-1-pyrenylamine derivative, N-Phenyl-N-(3-diphenylaminophenyl)-1-pyrenylamine derivatives for use in the above photoconductor, intermediates for producing the m-phenylenediamine derivatives, and methods of synthesizing these derivatives.

2. Discussion of Background

Conventionally, inorganic materials such as selenium, cadmium sulfide and zinc oxide are used as photoconductive materials for electrophotographic photoconductors in the electrophotographic process. The above-mentioned electrophotographic process is one of the image forming processes, through which the surface of the photoconductor is charged uniformly in the dark to a predetermined polarity, for instance, by corona charge. The uniformly charged photoconductor is exposed to a light image to selectively dissipate the electrical charge of the exposed areas, so that a latent electrostatic image is formed on the photoconductor. The thus formed latent electrostatic image is developed by toner particles comprising a coloring agent such as a dye and a pigment, and a binder agent such as a polymeric material, to a visible image.

Fundamental characteristics required for the photoconductor for use in such an electrophotographic process are: (1) chargeability to an appropriate potential in the dark, (2) minimum dissipation of electrical charge in the dark, (3) rapid dissipation of electrical charge when exposed to light, and (4) maintenance of a uniform photoconductive layer.

However, while the above-mentioned inorganic materials have many advantages, they have several shortcomings from the viewpoint of practical use.

For instance, a selenium photoconductor, which is widely used at present, satisfies the above-mentioned requirements (1) to (4) completely, but it has the shortcomings that its manufacturing conditions are difficult and, accordingly, its production cost is high. In addition, it is difficult to work it into the form of a belt due to its poor flexibility, and it is so vulnerable to heat and mechanical shocks that it must be handled with the utmost care.

A cadmium sulfide photoconductor and a zinc oxide photoconductor can be obtained by coating a dispersion of cadmium sulfide particles and zinc oxide particles respectively in a binder resin on a substrate. However, they are poor in mechanical properties, such as surface smoothness, hardness, tensile strength and wear resistance. Therefore, they cannot be used in the repeated operation.

To solve the problems of the inorganic materials, various electrophotographic photoconductors employing organic materials have been proposed recently and some are put to practical use. For example, there are known a photoconductor comprising poly-N-vinylcarbazole and 2,4,7 -trinitrofluorene-9-one, as disclosed in U.S. Pat. No. 3,484,237; a photoconductor prepared by sensitizing poly-N-vinylcarbazole with a pigment of pyrylium salt, as described in Japanese Patent Publication 48-25658; a photoconductor comprising as the main component an organic pigment, as described in Japanese Laid-Open Patent Application 47-37543; a photoconductor comprising as the main component an eutectic crystal complex of a dye and a resin, as described in Japanese Laid-Open Patent Application 47-10735; a photoconductor prepared by sensitizing a triphenylamine compound with a sensitizer pigment, as described in U.S. Pat. No. 3,180,730; a photoconductor comprising an amine derivative as a charge transporting material, as described in Japanese Laid-Open Patent Application 57-195254; a photoconductor comprising poly-N-vinylcarbazole and an amine derivative as charge transporting materials, as described in Japanese Laid-Open patent Application 58-1155; and a photoconductor comprising a polyfunctional tertiary amine compound, in particular benzidine compound, as a photoconductive material, as described in U.S. Pat. No. 3,265,496, Japanese Patent Publication 39-11546 and Japanese Laid-Open Patent Application 53-27033.

Furthermore, there are disclosed photoconductors employing m-phenylenediamine compounds, such as N,N,N',N' -tetraphenyl-m-phenylenediamine, as described in U.S. Pat. No. 3,265,496 and N,N,N',N'-tetra-substituted phenyl-m-phenylenediamine, as described in Japanese Laid-Open Patent Application 1-142642.

These electrophotographic photoconductors have their own excellent characteristics and considered to be valuable for practical use. With various requirements of the electrophotographic photoconductor in electrophotography taken into consideration, however, the above-mentioned conventional electrophotographic photoconductors cannot meet all the requirements for use in electrophotography.

SUMMARY OF THE INVENTION

It is therefore a first object of the present invention to provide an electrophotographic photoconductor free from the conventional shortcomings, which can completely satisfy all the requirements in the electrophotographic process, including high durability, and can be easily manufactured at relatively low cost.

A second object of the present invention is to provide novel N-phenyl-N-(3-diphenylaminophenyl)-1-pyrenylamine derivatives serving as photoconductive materials for use in the above-mentioned electrophotographic photoconductor.

A third object of the present invention is to provide methods of preparing the above novel N-phenyl-N-(3-diphenylaminophenyl)-1 -pyrenylamine derivatives.

A fourth object of the present invention is to provide intermediates for producing the N-phenyl-N-(3-diphenylaminophenyl)- 1-pyrenylamine derivatives.

A fifth object of the present invention is to provide methods of producing the intermediates.

The first object of the present invention can be achieved by an electrophotographic photoconductor comprising an electroconductive substrate and a photoconductive layer formed thereon comprising a m-phenylenediamine derivative of formula (I):

(I)

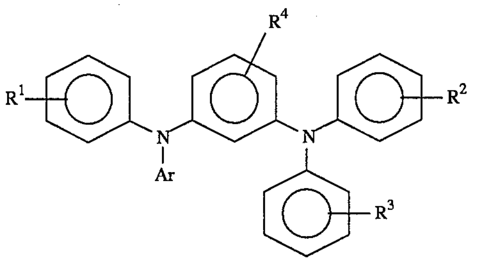

wherein Ar represents a non-condensed polycyclic hydrocarbon group having not more than 18 carbon atoms other than a phenyl group, or a condensed polycyclic hydrocarbon group having not more than 18 carbon atoms; and $R^1$, $R^2$, $R^3$ and $R^4$ each represent hydrogen, a halogen atom, a cyano group, a nitro group, an alkyl group having 1 to 12 carbon atoms, an alkoxyl group having 1 to 12 carbon atoms, an aryl group selected from the group consisting of phenyl group, biphenyl group, and naphthyl group, an aryloxy group with an aryl group selected from the group consisting of phenyl group and naphthyl group, an alkylmercapto group represented by $—SR^5$ in which $R^5$ represents an alkyl group having 1 to 12 carbon atoms, a group represented by

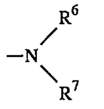

in which $R^6$ and $R^7$ each represent hydrogen, an alkyl group having 1 to 12 carbon atoms, or an aryl group selected from the group consisting of phenyl group, biphenyl group, and naphthyl group, an alkylenedioxy group or an alkylenedithio group.

The first object of the present invention can also be achieved by use of a N-phenyl-N-(3-aminophenyl)-1-pyrenylamine derivative of formula (III) instead of the m-phenylenediamine derivative in the above photoconductor:

(III)

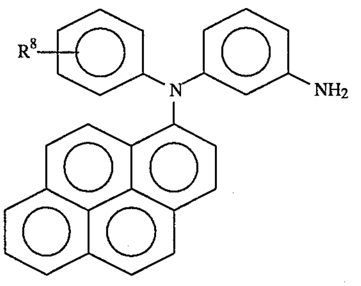

wherein $R^8$ represents hydrogen, an alkyl group having 1 to 12 carbon atoms, an alkoxyl group having 1 to 12 carbon atoms, or a phenyl group.

The second object of the present invention can be achieved by N-phenyl-N-(3-diphenylaminophenyl)-1-pyrenylamine derivatives of formula (II):

(II)

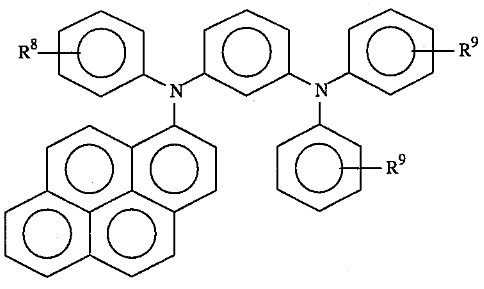

wherein $R^8$ and $R^9$ each represent hydrogen, an alkyl group having 1 to 12 carbon atoms, an alkoxyl group having 1 to 12 carbon atoms, or a phenyl group.

The third object of the present invention can be achieved by a method of preparing the above-mentioned N-phenyl-N-(3-diphenylaminophenyl)-1-pyrenylamine derivative of formula (II) comprising the step of allowing an N-phenyl-N-( 3-aminophenyl)-1-pyrenylamine derivative of formula (III) to react with a halogenated benzene derivative of formula (IV):

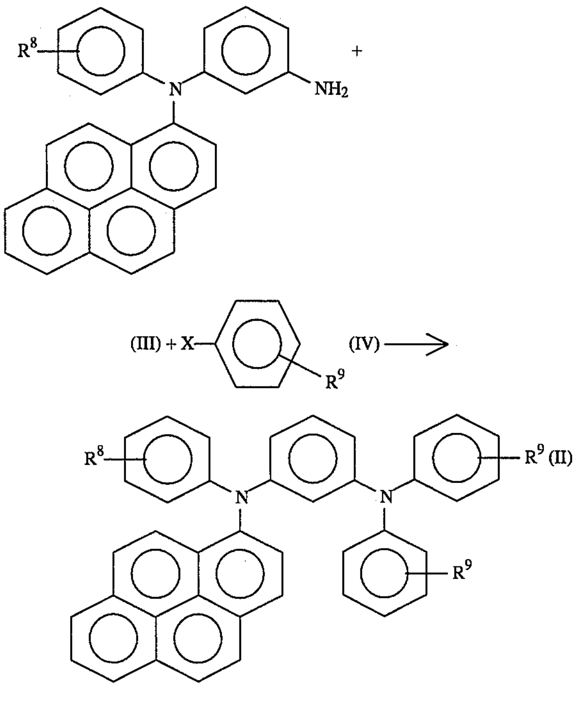

wherein $R^8$ and $R^9$ are the same as defined above; and X represents bromine or iodine.

The fourth object of the present invention can be achieved by the above-mentioned N-phenyl-N-(3-aminophenyl)-1-pyrenylamine derivative of formula (III) and a corresponding N-phenyl-N-(3-nitrophenyl)-1-pyrenylamine derivative.

The fifth object of the present invention can be achieved by producing the N-phenyl-N-(3-nitrophenyl)-1 -pyrenylamine derivative by allowing a nitrodiphenylamine derivative of formula (IX) to react with 1-halogenopyrene of formula (X),

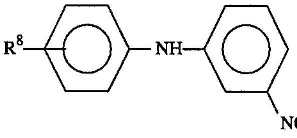

(IX) +

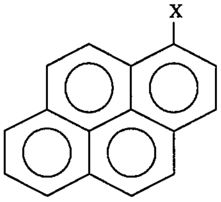

(X)

and reducing the N-phenyl-N-(3-nitrophenyl)-1-pyrenylamine derivative to produce the N-phenyl-N-(3-aminophenyl)-1 -pyrenylamine derivative.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
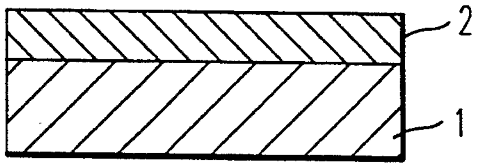
FIG. 1 is a schematic cross-sectional view of a first example of an electrophotographic photoconductor according to the present invention.

In the present invention, an electrophotographic photoconductor comprises an electroconductive substrate and a photoconductive layer formed thereon comprising a m-phenylenediamine derivative of formula (I):

(I)

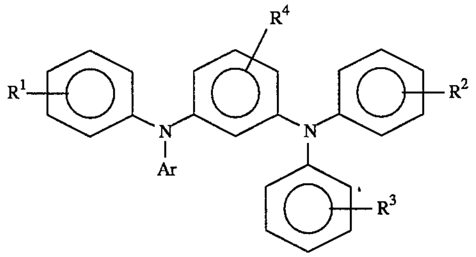

wherein Ar represents a non-condensed polycyclic hydrocarbon group having not more than 18 carbon atoms other than a phenyl group, or a condensed polycyclic hydrocarbon group having not more than 18 carbon atoms; and $R^1$, $R^2$, $R^3$ and $R^4$ each represent hydrogen, a halogen atom, a cyano group, a nitro group, an alkyl group having 1 to 12 carbon atoms, an alkoxyl group having 1 to 12 carbon atoms, an aryl group selected from the group consisting of phenyl group, biphenyl group, and naphthyl group, an aryloxy group with an aryl group selected from the group consisting of phenyl group and naphthyl group, an alkylmercapto group represented by $—SR^5$ in which $R^5$ represents an alkyl group having 1 to 12 carbon atoms, an group represented by

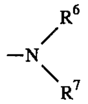

in which $R^6$ and $R^7$ each represent hydrogen, an alkyl group having 1 to 12 carbon atoms, or an aryl group-selected from the group consisting of phenyl group, biphenyl group, and naphthyl group, an alkylenedioxy group or an alkylenedithio group.

The m-phenylenediamine derivative of formula (I) for use in the photoconductive layer of the electrophotographic photoconductor according to the present invention can be prepared by allowing an amine derivative of formula (V) to react with a halogenated benzene derivative of formula (IV) or formula (IV-a):

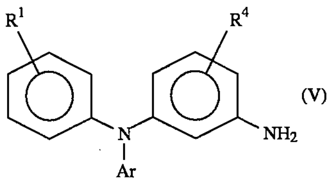

(V) +

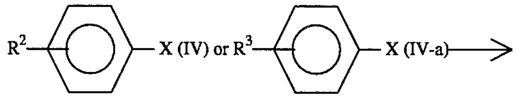

(IV) or (IV-a)

-continued

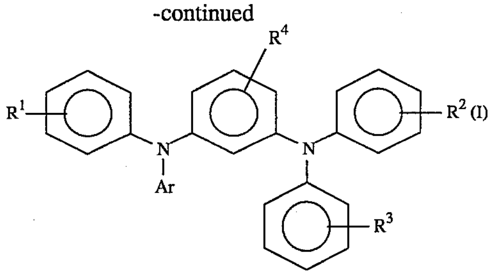

wherein Ar, $R^1$, $R^2$, $R^3$ and $R^4$ are the same as defined above; and X represents bromine or iodine.

The m-phenylenediamine derivative of formula (I) can also be prepared by allowing a halide of formula (VI) to react with a diphenylamine derivative of formula (VII):

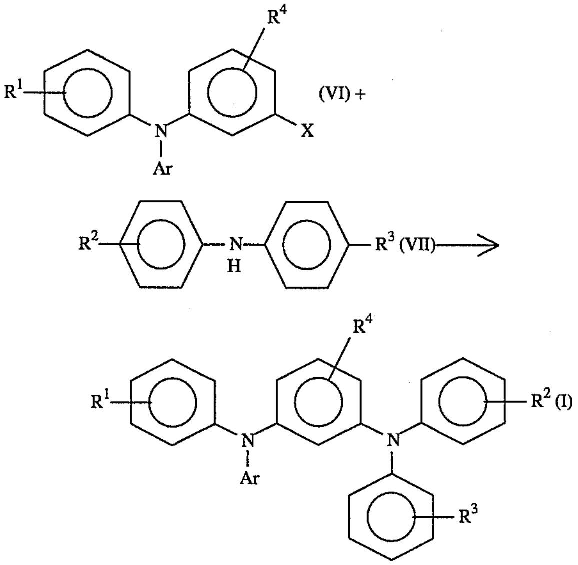

wherein Ar, $R^1$, $R^2$, $R^3$, $R^4$ and X are the same as defined above.

Specific examples of the non-condensed polycyclic hydrocarbon group not more than 18 carbon atoms other than a phenyl group represented by Ar in formulas (I), (V), and (VI) are biphenyl group, terphenyl group, and phenoxyphenyl group. Specific examples of the condensed polycyclic hydrocarbon group having not more than 18 carbon atoms represented by Ar are pentalenyl group, indenyl group, naphthyl group, azulenyl group, heptalenyl group, biphenylenyl group, as-indacenyl group, fluorenyl group, S-indacenyl group, acenaphthylenyl group, pleiadenyl group, acenaphthenyl group, phenalenyl group, phenanthryl group, anthryl group, fluoranthenyl group, acephenanthrylenyl group, aceanthrylenyl group, triphenylenyl group, pyrenyl group, chrysenyl group and naphthacenyl group.

Furthermore, the above-mentioned non-condensed polycyclic hydrocarbon group other than a phenyl group or condensed polycyclic hydrocarbon group may have a substituent. Examples of the substituent are as follows: (1) A halogen atom, a cyano group and a nitro group. (2) A straight chain or branched chain alkyl group having 1 to 12 carbon atoms, more preferably an alkyl group having 1 to 8 carbon atoms, and further preferably an alkyl group having 1 to 4 carbon atoms, which may have a substituent.

Specific examples of the above alkyl group include methyl group, ethyl group, n-propyl group, i-propyl group, t-butyl group, s-butyl group, n-butyl group, i-butyl group, 2-hydroxyethyl group, 2-cyanoethyl group, 2-ethoxyethyl group, 2-methoxyethyl group, benzyl group, 4-chlorobenzyl group, 4-methylbenzyl group, 4-methoxybenzyl group and 4-phenylbenzyl group.

Specific examples of the substituent of the above alkyl group are hydroxyl group, cyano group, alkoxyl group having 1 to 4 carbon atoms, phenyl group, a halogen atom, phenyl group substituted with alkyl group having 1 to 4 carbon atoms, and phenyl group substituted with alkoxyl group having 1 to 4 carbon atoms.

(3) An alkoxyl group represented by $—OR^5$, in which $R^5$ represents the same alkyl group which may have a substituent as defined in (2).

Specific examples of the above alkoxyl group include methoxy group, ethoxy group, n-propoxy group, i-propoxy group, t-butoxy group, n-butoxy group, s-butoxy group, i-butoxy group, 2-hydroxyethoxy group, 2-cyanoethoxy group, benzyloxy group and 4-methylbenzyloxy group.

(4) An aryloxy group, in which an aryl group represents, for example, a phenyl group and a naphthyl group. The above aryloxy group may have a substituent such as an alkoxyl group having 1 to 4 carbon atoms, an alkyl group having 1 to 4 carbon atoms or a halogen atom.

Specific examples of the above aryloxy group include phenoxy group, 1-naphthyloxy group, 2-naphthyloxy group, 4-methylphenoxy group, 4-methoxyphenoxy group, 4-chlorophenoxy group and 6-methyl-2-naphthyloxy group.

(5) An alkylmercapto group represented by $—SR^5$, in which $R^5$ represents the same alkyl group which may have a substituent as defined in (2).

Specific examples of the above alkylmercapto group include methylthio group, ethylthio group, phenylthio group and p-methylphenylthio group.

(6)

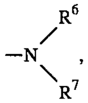

in which $R^6$ and $R^7$ independently represent hydrogen, the same alkyl group which may have a substituent as defined in (2) or an aryl group which may have a substituent. As the aryl group, phenyl group, biphenyl group or naphthyl group can be employed, which may have a substituent such as an alkoxyl group having 1 to 4 carbon atoms, an alkyl group having 1 to 4 carbon atoms or a halogen atom. $R^6$ and $R^7$ may form a ring in combination, or in combination with carbon atoms on the aryl group.

Specific examples of the above

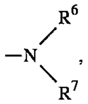

in which $R^6$ and $R^7$ independently represent, include an amino group, diethylamino group, N-methyl-N-phenylamino group, N,N-diphenylamino group, N,N-di(p-tolyl)amino group, dibenzylamino group, piperidino group, morpholino group and julolidyl group.

(7) An alkylenedioxy group such as methylenedioxy group, or an alkylenedithio group such as methylenedithio group.

Specific examples of the alkyl group, alkoxyl group, aryl group, aryloxy group, alkylmercapto group, amino group, alkylenedioxy group and alkylenedithio group represented by $R^1$, $R^2$, $R^3$ and $R^4$ in formula (I) are the same as mentioned in (2) to (7). It is preferable that the above-mentioned alkyl group and alkoxyl group have 1 to 12 carbon atoms, more preferably 1 to 8 carbon atoms, and further preferably 1 to 4 carbon atoms.

Specific examples of the m-phenylenediamine derivatives of formula (I) are shown in the following Table 1:

TABLE 1

| Compound No. | Ar | $R^1$ | $R^2$ | $R^3$ | $R^4$ |
|---|---|---|---|---|---|
| 1 | 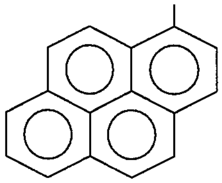 | H | H | H | H |
| 2 | Same as above | H | $3-CH_3$ | H | H |
| 3 | Same as above | H | $4-CH_3$ | H | H |
| 4 | Same as above | H | $4-OCH_3$ | H | H |
| 5 | Same as above | H | $3-CH_3$ | $3-CH_3$ | H |
| 6 | Same as above | H | $4-CH_3$ | $4-CH_3$ | H |
| 7 | Same as above | H | $4-OCH_3$ | $4-OCH_3$ | H |
| 8 | Same as above | H | $4-C_6H_5$ | $4-CH_3$ | H |
| 9 | Same as above | $4-CH_3$ | H | H | H |
| 10 | Same as above | $4-CH_3$ | $3-CH_3$ | H | H |
| 11 | Same as above | $4-CH_3$ | $4-CH_3$ | H | H |
| 12 | Same as above | $4-CH_3$ | $4-CH_3$ | $4-CH_3$ | H |
| 13 | Same as above | $4-CH_3$ | $4-CH_3$ | $4-OCH_3$ | H |
| 14 | Same as above | $4-CH_3$ | $4-OCH_3$ | $4-OCH_3$ | H |
| 15 | Same as above | $2-CH_3$ | $4-C_6H_5$ | $4-C_6H_5$ | H |
| 16 | Same as above | $3-CH_3$ | $4-CH_3$ | $4-CH_3$ | H |
| 17 | Same as above | $3-CH_3$ | $3-CH_3$ | $3-CH_3$ | H |
| 18 | Same as above | $4-OCH_3$ | H | H | H |
| 19 | Same as above | $4-OCH_3$ | $4-CH_3$ | $4-CH_3$ | H |
| 20 | Same as above | $4-OCH_3$ | $3-CH_3$ | H | $5-CH_3$ |
| 21 | 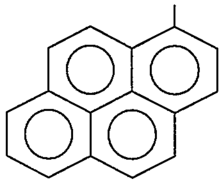 | $4-OCH_3$ | $4-OCH_3$ | $4-OCH_3$ | H |
| 22 | Same as above | $4-OCH_3$ | $2-CH_3$ | $2-CH_3$ | H |
| 23 | Same as above | $4-SCH_3$ | $4-CH_3$ | $4-OCH_3$ | H |
| 24 | Same as above | $3-OC_6H_5$ | $4-CH_3$ | H | H |
| 25 | Same as above | H | H | H | $5-N(C_2H_5)_2$ |
| 26 | Same as above | 4-Cl | 4-Cl | 4-Cl | H |
| 27 | Same as above | $4-CH_3$ | 4-CN | H | H |
| 28 | Same as above | $4-OC_2H_5$ | $3-NO_2$ | $3-NO_2$ | H |
| 29 | Same as above | $4-C_6H_4CH_3(P)$ | $4-CH_3$ | $4-CH_3$ | H |
| 30 | 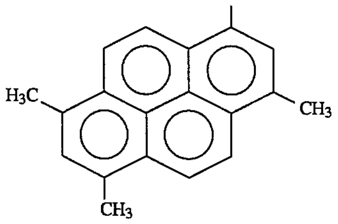 | H | H | H | H |
| 31 | Same as above | $4-CH_3$ | $4-CH_3$ | $4-CH_3$ | H |
| 32 | Same as above | $3-CH_3$ | $4-OCH_3$ | $4-CH_3$ | H |
| 33 | Same as above | $3-CH_3$ | $2-C_2H_5$ | $2-C_2H_5$ | H |
| 34 | 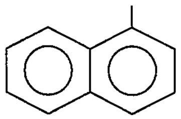 | H | H | H | H |

TABLE 1-continued
| Compound No. | Ar | $R^1$ | $R^2$ | $R^3$ | $R^4$ |
| --- | --- | --- | --- | --- | --- |
| 35 | 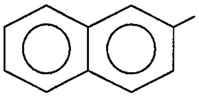 | 4-$C_2H_5$ | 4-$C_2H_5$ | 4-$C_2H_5$ | 5-$CH_3$ |
| 36 | 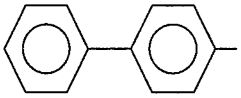 | 4-$CH_3$ | 4-$CH_3$ | 4-$CH_3$ | H |
| 37 | Same as above | H | H | H | H |
| 38 | 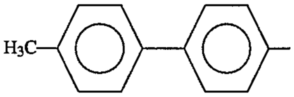 | 4-$CH_3$ | 4-$CH_3$ | 4-$CH_3$ | H |
| 39 | 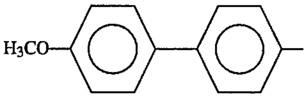 | 4-$CH_3$ | 4-$CH_3$ | 4-$CH_3$ | H |
| 40 | 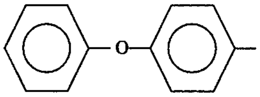 | 4-$CH_3$ | 4-$CH_3$ | 4-$CH_3$ | H |
| 41 | 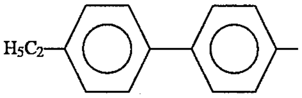 | 4-$CH_3$ | 4-$CH_3$ | 4-$CH_3$ | H |
| 42 | 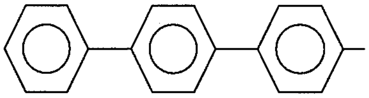 | 4-$C_2H_5$ | 3-$CH_3$ | 3-$CH_3$ | H |
| 43 | 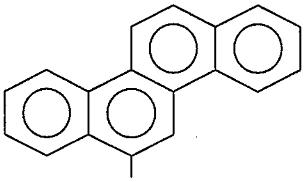 | 2-$CH_3$ | 3-$C_2H_5$ | H | H |
| 44 | 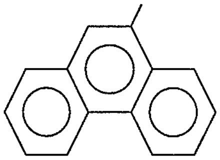 | 4-$C_6H_4CH_3$(P) | 4-t$C_4H_9$ | 4-t$C_4H_9$ | H |
| 45 | 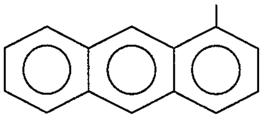 | H | 3,4-$CH_2O_2$ | 3,4-$CH_2O_2$ | H |
| 46 | 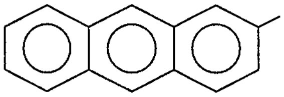 | 2-$OC_2H_5$ | 4-$NO_2$ | H | H |
| 47 | 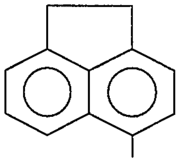 | H | H | 3-$CH_3$ | H |

TABLE 1-continued

| Compound No. | Ar | $R^1$ | $R^2$ | $R^3$ | $R^4$ |
|---|---|---|---|---|---|
| 48 | 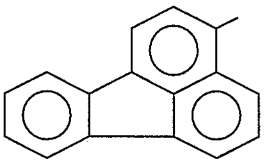 | 3-$C_2H_5$ | 4-$CH_2C_6H_5$ | 4-$CH_2C_6H_5$ | H |
| 49 | 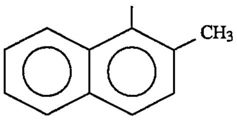 | 4-n$C_4H_9$ | 4-$OCH_3$ | 4-$OCH_3$ | H |

Among the above-mentioned m-phenylenediamine derivatives, Compound Nos. 1, 5, 6, 7, 9, 12, 14, 15, 16, 17, 18, 19, 21 and 22 are novel N-phenyl-N-(3-diphenylaminophenyl)- 1-pyrenylamine derivatives which are represented by formula (II) and usable as photoconductive materials.

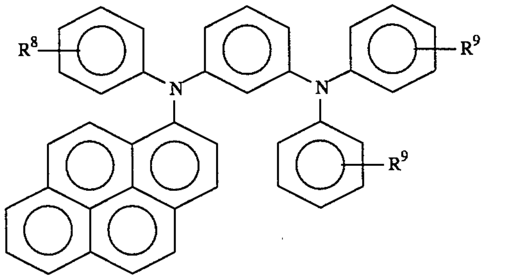

(II)

wherein $R^8$ and $R^9$ each represent hydrogen, an alkyl group having 1 to 12 carbon atoms, an alkoxyl group having 1 to 12 carbon atoms, or a phenyl group.

The above-mentioned N-phenyl-N-(3-diphenylaminophenyl)-1 -pyrenylamine derivative of formula (II) can be prepared by allowing an N-phenyl-N-(3-aminophenyl)-1-pyrenylamine derivative of formula (III) to react with a halogenated benzene derivative of formula (IV):

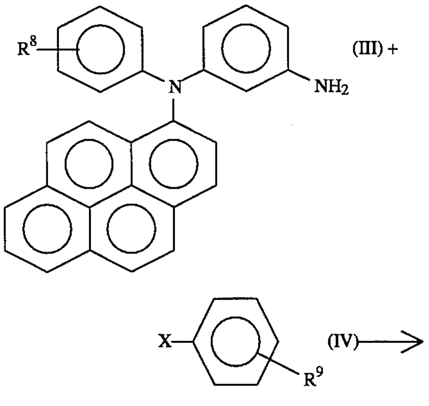

(III) +

(IV)

-continued

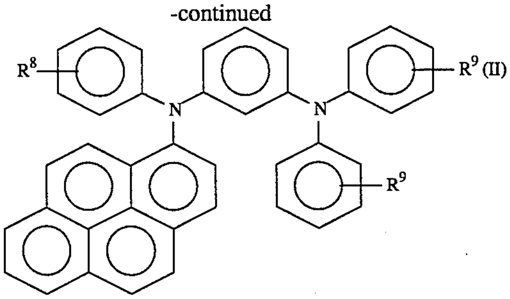

(II)

wherein $R^8$ and $R^9$ are the same as defined above; and X represents bromine or iodine.

The above-mentioned reaction between the N-phenyl-N-( 3-aminophenyl)-1-pyrenylamine derivative and the halogenated benzene derivative for preparing the N-phenyl-N-( 3-diphenylaminophenyl)-1-pyrenylamine derivative can be carried out in a solvent or without a solvent in an atmosphere of nitrogen at about 150° to 250° C. in the presence of copper powder, copper oxide or copper halogenide, with an alkaline material added thereto in a sufficient amount for neutralizing hydrogen halogenide generated in the course of the reaction.

Examples of the above-mentioned alkaline material used in the reaction are sodium hydroxide, potassium hydroxide, sodium carbonate and potassium carbonate. Examples of the solvent used in the reaction are nitrobenzene, dichlorobenzene, quinoline, N,N-dimethylformamide, dimethyl sulfoxide, N-methylpyrrolidone and 1,3-dimethyl-2 -imidazolidinone.

The alkyl group represented by $R^8$ and $R^9$ in formulas (II), (III), and (IV) is an alkyl group having 1 to 12 carbon atoms, preferably 1 to 8 carbon atoms, more preferably 1 to 4 carbon atoms such as methyl group, ethyl group, propyl group and butyl group.

The alkoxyl group represented by $R^8$ and $R^9$ is an alkoxyl group having 1 to 12 carbon atoms, preferably 1 to 8 carbon atoms, more preferably 1 to 4 carbon atoms such as methoxy group, ethoxy group and propoxy group.

The above-mentioned alkyl group and alkoxyl group may have a substituent such as a phenyl group, a halogen atom, an alkoxyl group and an aryloxy group.

The phenyl group represented by $R^8$ and $R^9$ also may have a substituent such as an alkyl group having 1 to 8 carbon atoms, preferably 1 to 4 carbon atoms, for instance, methyl group, ethyl group, propyl group and butyl group; an alkoxyl group having 1 to 8 carbon atoms, preferably 1 to 4 carbon atoms, for instance, methoxy group, ethoxy group and propoxy group; and a halogen atom, for instance, bromine, chlorine and fluorine.

The above-mentioned novel N-phenyl-N-(3-diphenylaminophenyl)- 1-pyrenylamine derivative of formula (II) according to the present invention, which is remarkably effective as a photoconductive material in the electrophotographic photoconductor, is optically or chemically sensitized with a sensitizer such as a dye or Lewis acid. In addition, the N-phenyl-N-(3-diphenylaminophenyl)-1-pyrenylamine derivative effectively functions as a charge transporting material in a function-separating type electrophotographic photoconductor where an organic or inorganic pigment serves as a charge generating material.

The previously mentioned N-phenyl-N-(3-aminophenyl)-1 -pyrenylamine derivative of formula (III) which can be used in the reaction for preparing the N-phenyl-N-(3-diphenylaminophenyl)- 1-pyrenylamine derivative of formula (II) is also a novel compound and usable as a photoconductive material.

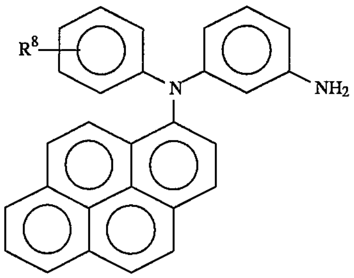

(III)

wherein $R^8$ represents hydrogen, an alkyl group having 1 to 12 carbon atoms, an alkoxyl group having 1 to 12 carbon atoms, or a phenyl group.

The N-phenyl-N-(3-aminophenyl)-1-pyrenylamine derivative of formula (III) can be prepared by reducing an N-phenyl-N-(3-nitrophenyl)-1-pyrenylamine derivative of formula (VIII):

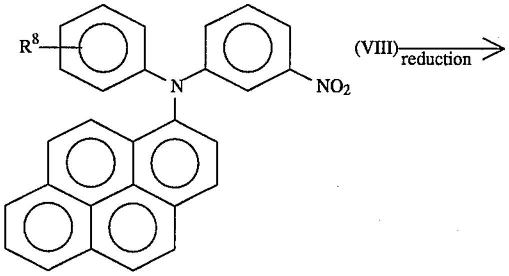

-continued

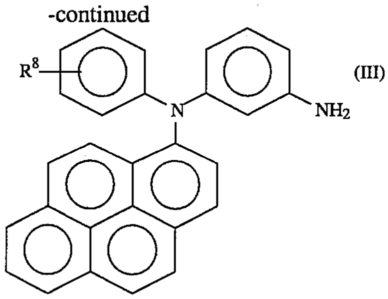

(III)

wherein $R^8$ is the same as defined above.

The N-phenyl-N-(3-nitrophenyl)-1-pyrenylamine derivative can be reduced to the N-phenyl-N-(3-aminophenyl)-1-pyrenylamine derivative, for example, with a hydrogenation method. In this case, as a catalyst, platinum oxide, Raney nickel, and platinum, palladium, rhodium, and ruthenium, which are carried by activated carbon, alumina, or barium sulfate can be employed.

The above reduction reaction is carried out in a closed system by replacing a gas phase with a hydrogen gas having 1 atmospheric pressure with vigorously stirring. The hydrogen gas is supplied through a reduction valve in an equivalent amount with that of the absorbed hydrogen gas. The reaction is completed when a stoichiometric amount of the hydrogen gas is absorbed and the absorption of the hydrogen gas is stopped. In this case, the reaction can be carried but at room temperature. In the case where the hydrogen gas is slowly absorbed, the reaction can be carried out under the application of heat. As the solvent used in the reaction, methanol, ethanol, propanol, tetrahydrofuran, dioxane, ethyl acetate, and N,N-dimethylformamide can be employed.

The reduction reaction can also be carried out in an organic solvent under application of heat using as a reducing agent iron-hydrochloric acid or tin tetrachloride-hydrochloric acid. In this case, it is preferable that the reaction be carried out at 70° to 120° C., and the reaction is completed in about 0.5 to 3 hours. In the case where iron-hydrochloric acid is used as the reducing agent, it is preferable that the reaction be carried out using N,N-dimethylformamide as a solvent.

The previously mentioned N-phenyl-N-(3-nitrophenyl)-1 -pyrenylamine derivative of formula (VIII) which is used in the reduction reaction for preparing the N-phenyl-N-(3-aminophenyl)-1-pyrenylamine derivative of formula (III) is also a novel compound.

(VIII)

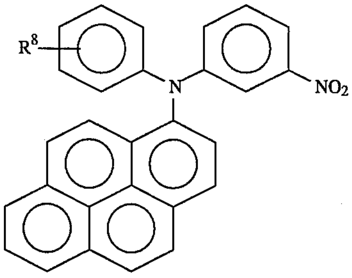

wherein $R^8$ represents hydrogen, an alkyl group having 1 to 12 carbon atoms, an alkoxyl group having 1 to 12 carbon atoms, or a phenyl group.

The N-phenyl-N-(3-nitrophenyl)-1-pyrenylamine derivative can be prepared by allowing a 3-nitrodiphenylamine derivative of formula (IX) to react with 1-halogenopyrene of formula (X):

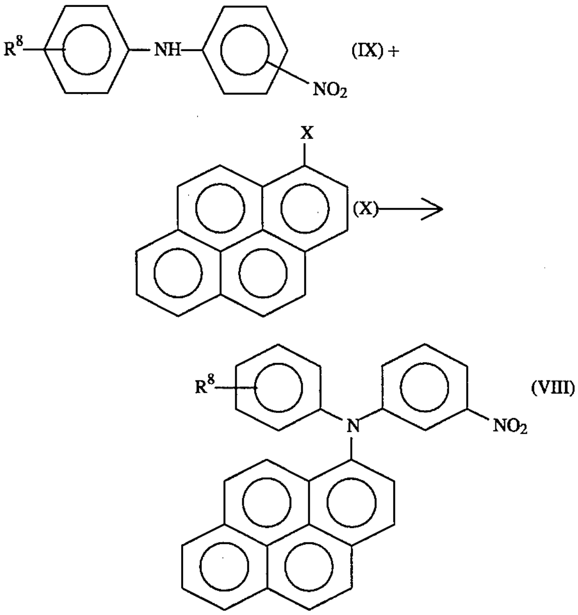

(IX) +

(X)

(VIII)

wherein $R^8$ is the same as defined above; and X represents bromine or iodine.

The above-mentioned reaction between the 3-nitrodiphenylamine derivative and 1-halogenopyrene for preparing the N-Phenyl-N-(3-nitrophenyl)-1-pyrenylamine derivative can be carried out in a solvent or without a solvent in an atmosphere of nitrogen at about 150° to 250° C. in the presence of copper powder, copper oxide or copper halogenide, with an alkaline material added thereto in a sufficient amount for neutralizing hydrogen halogenide generated in the course of the reaction.

Examples of the above-mentioned alkaline material used in the reaction are the same as mentioned previously.

Specific examples of the alkyl group, alkoxyl group and phenyl group represented by $R^8$ in formulas (VIII) and (IX) are the same as those represented by $R^8$ in formulas (II) and (III).

The structure of the photoconductor of the present invention will now be explained making reference to FIGS. 1 to 5.

In the photoconductors according to the present invention, one or more of m-phenylenediamine derivatives of formula (I) are contained in the photoconductive layers 2, 2*a*, 2*b*, 2*c* and 2*d*. The m-phenylenediamine derivatives can be employed in different ways, for example, as shown in FIGS. 1 to 5.

In the photoconductor as shown in FIG. 1, a photoconductive layer 2 is formed on an electroconductive substrate 1, which photoconductive layer 2 comprises a m-phenylenediamine derivative, a sensitizing dye and a binder agent (binder resin). In this photoconductor, the m-phenylenediamine derivative works as a photoconductive material, through which charge carriers which are necessary for the light decay of the photoconductor are generated and transported. However, the m-phenylenediamine derivative itself scarcely absorbs light in the visible light range, so that it is necessary to add a sensitizing dye which absorbs light in the visible light range in order to form latent electrostatic images by use of visible light.

Figure 2:
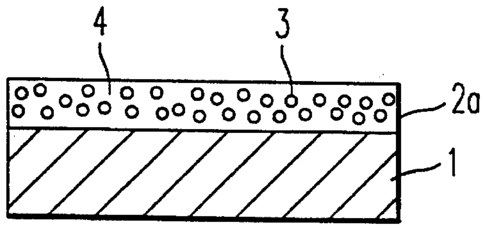
FIG. 2 is a schematic cross-sectional view of a second example of an electrophotographic photoconductor according to the present invention.

Referring to FIG. 2, there is shown a cross-sectional view of another embodiment of an electrophotographic photoconductor according to the present invention. In the figure, on the electroconductive substrate 1, there is formed a photoconductive layer 2*a* comprising a charge generating material 3 dispersed in a charge transporting medium 4 comprising a m-phenylenediamine derivative and a binder agent. In this embodiment, the m-phenylenediamine derivative and the binder agent (or a mixture of the binder agent and a plasticizer) in combination constitute the charge transporting medium 4. The charge generating material 3, which is, for example, an inorganic or organic pigment, generates charge carriers. The charge transporting medium 4 accepts the charge carriers generated by the charge generating material 3 and transports those charge carriers.

In this electrophotographic photoconductor, it is essential that the light-absorption wavelength regions of the charge generating material 3 and the m-phenylenediamine derivative not overlap in the visible light range. This is because, in order to have the charge generating material 3 produce charge carriers efficiently, it is necessary to allow the light to reach the surface of the charge generating material 3. The m-phenylenediamine derivatives of formula (I) scarcely absorb the light in the visible range. Therefore, especially when combined with the charge generating material 3 which absorbs the light in the visible region and generates charge carriers, the m-phenylenediamine derivatives can work effectively as charge transporting materials.

Figure 3:
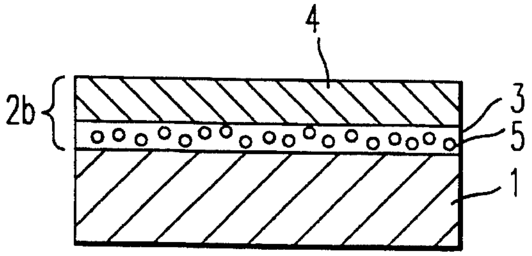
FIG. 3 is a schematic cross-sectional view of a third example of an electrophotographic photoconductor according to the present invention.

Referring to FIG. 3, there is shown a cross-sectional view of a further embodiment of an electrophotographic photoconductor according to the present invention. In the figure, there is formed on an electroconductive substrate 1 a two-layered photoconductive layer 2*b* comprising a charge generation layer 5 containing a charge generating material 3, and a charge transport layer 4 containing a m-phenylenediamine derivative.

In this photoconductor, the light which has passed through the charge transport layer 4 reaches the charge generation layer 5, where charge carriers are generated. The charge carriers which are necessary for the light decay for latent electrostatic image formation are generated by the charge generating material 3, and accepted and transported by the charge transport layer 4. In the charge transport layer 4, the m-phenylenediamine derivative mainly works for transportation of the charge carriers. The generation and transportation of the charge carriers are performed by the same mechanism as that in the photoconductor shown in FIG. 2.

Figure 4:
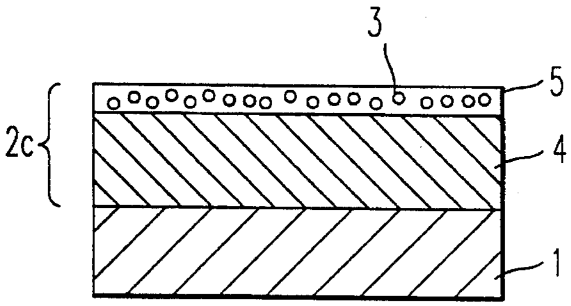
FIG. 4 is a schematic cross-sectional view of a fourth example of an electrophotographic photoconductor according to the present invention.

Referring to FIG. 4, there is shown still another embodiment of an electrophotographic photoconductor according to the present invention. In the figure, the overlaying order of a charge generation layer 5 and a charge transport layer 4 is reversed. The mechanism of the generation and transportation of charge carriers is substantially the same as that of the photoconductor shown in FIG. 3.

Figure 5:
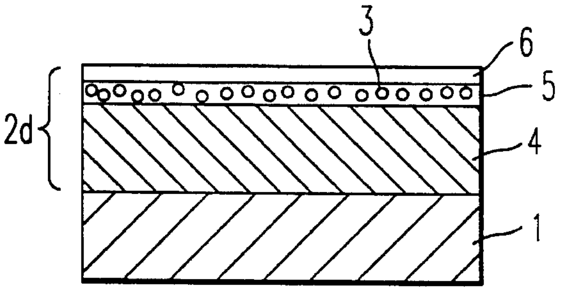
FIG. 5 is a schematic cross-sectional view of a fifth example of an electrophotographic photoconductor according to the present invention.

In the above photoconductor, a protective layer 6 may be formed on a charge generation layer 5 as shown in FIG. 5 for improving the mechanical strength thereof.

When the electrophotographic photoconductor according to the present invention as shown in FIG. 1 is prepared, one or more of m-phenylenediamine derivatives of formula (I) are dispersed in a binder resin solution, and a sensitizing dye is then added to the mixture, so that a photoconductive layer coating liquid is prepared. The thus prepared photoconductive layer coating liquid is coated on the electroconductive substrate 1 and dried, so that the photoconductive layer 2 is formed on the electroconductive substrate 1.

It is preferable that the thickness of the photoconductive layer 2 be in the range of 3 to 50 μm, more preferably in the range of 5 to 20 μm. It is preferable that the amount of the m-phenylenediamine derivative contained in the photoconductive layer 2 be in the range of 30 to 70 wt. %, more preferably about 50 wt. %.

It is preferable that the amount of the sensitizing dye contained in the photoconductive layer 2 be in the range of 0.1 to 5 wt. %, more preferably in the range of 0.5 to 3 wt. %.

Specific examples of the sensitizing dye for use in the present invention are as follows: triarylmethane dyes such as Brilliant Green, Victoria Blue B, Methyl Violet, Crystal Violet and Acid Violet 6B; xanthene dyes such as Rhodamine B, Rhodamine 6G, Rhodamine G Extra, Eosin S, Erythrosin, Rose Bengale and Fluoresceine; thiazine dyes such as Methylene Blue; cyanine dyes such as cyanin; and pyrylium dyes such as 2,6-diphenyl-4-(N,N-dimethylaminophenyl)thiapyrylium perchlorate and benzopyrylium salts (described in Japanese Patent Publication 48-25658). These sensitizing dyes can be used alone or in combination.

The electrophotographic photoconductor shown in FIG. 2 can be obtained by dispersing finely-divided particles of the charge generating material 3 in the solution in which one or more of m-phenylenediamine derivatives and the binder agent are dissolved, coating the above-prepared dispersion on the electroconductive substrate 1 and then drying the same to form the photoconductive layer **2*a***.

It is preferable that the thickness of the photoconductive layer **2*a* be in the range of 3 to 50 μm, more preferably in the range of 5 to 20 μm. It is preferable that the amount of the m-phenylenediamine derivative contained in the photoconductive layer 2*a*** be in the range of 10 to 95 wt. %, more preferably in the range of 30 to 90 wt. %.

It is preferable that the amount of the charge generating material 3 contained in the photoconductive layer **2*a*** be in the range of 0.1 to 50 wt. %, more preferably in the range of 1 to 20 wt. %.

Specific examples of the charge generating material 3 are as follows: inorganic pigments such as selenium, selenium-tellurium, cadmium sulfide, cadmium sulfide-selenium and α-silicone; and organic pigments, such as C.I. Pigment Blue 25 (C.I. 21180), C.I. Pigment Red 41 (C.I. 21200), C.I. Acid Red 52 (C.I. 45100), and C.I. Basic Red 3 (C.I. 45210); an azo pigment having a carbazole skeleton (Japanese Laid-Open Patent Application 53-95033), an azo pigment having a distyryl benzene skeleton (Japanese Laid-Open Patent Application 53-133445), an azo pigment having a triphenylamine skeleton (Japanese Laid-Open Patent Application 53-132347), an azo pigment having a dibenzothiophene skeleton (Japanese Laid-Open Patent Application 54-21728), an azo pigment having an oxadiazole skeleton (Japanese Laid-Open Patent Application 54-12742), an azo pigment having a fluorenone skeleton (Japanese Laid-Open Patent Application 54-22834), an azo pigment having a bisstilbene skeleton (Japanese Laid-Open Patent Application 54-17733), an azo pigment having a distyryl oxadiazole skeleton (Japanese Laid-Open Patent Application 54-2129), and an azo pigment having a distyryl carbazole skeleton (Japanese Laid-Open Patent Application 54-14967); a phthalocyanine pigment such as C.I. Pigment Blue 16 (C.I. 74100); indigo pigments such as C.I. Vat Brown 5 (C.I. 73410) and C.I. Vat Dye (C.I. 73030); and perylene pigments such as Algol Scarlet B (made by Bayer Co., Ltd.) and Indanthrene Scarlet R (made by Bayer Co., Ltd.). These charge generating materials may be used alone or in combination.

The electrophotographic photoconductor shown in FIG. 3 can be obtained as follows:

The charge generating material is vacuum-deposited on the electroconductive substrate 1, or the dispersion in which finely-divided particles of the charge generating material 3 are dispersed in an appropriate solvent, together with the binder agent when necessary, is coated on the electroconductive substrate 1 and dried, so that the charge generation layer 5 is formed. When necessary, the charge generation layer 5 is subjected to surface treatment by buffing and adjustment of the thickness thereof. On the thus formed charge generation layer 5, a coating liquid in which one or more of m-phenylenediamine derivatives and the binder agent are dissolved is coated and dried, so that the charge transport layer 4 is formed. In the charge generation layer 5, the same charge generating material as employed in the previously mentioned photoconductive layer a can be used.

The thickness of the charge generation layer 5 is 5 μm or less, more preferably 2 μm or less. It is preferable that the thickness of the charge transport layer 4 be in the range of 3 to 50 μm, more preferably in the range of 5 to 20 μm. When the charge generation layer 5 is obtained by coating the dispersion in which finely-divided particles of the charge generating material 3 are dispersed in the binder agent, it is preferable that the amount of finely-divided particles of the charge generating material 3 contained in the charge generation layer 5 be in the range of 10 to 95 wt. %, more preferably in the range of about 50 to 90 wt. %. It is preferable that the amount of the m-phenylenediamine derivative contained in the charge transport layer 4 be in the range of 10 to 95 wt. %, more preferably in the range of 30 to 90 wt. %.

The electrophotographic photoconductor shown in FIG. 4 can be obtained as follows:

A coating liquid in which the m-phenylenediamine derivative and the binder agent are dissolved is coated on the electroconductive substrate 1 and dried to form the charge transport layer 4. On the thus formed charge transport layer 4, a dispersion prepared by dispersing finely-divided particles of the charge generating material 3 in the solvent, in which the binder agent is dissolved when necessary, is coated by spray coating and dried to form the charge generation layer 5 on the charge transport layer 4. The respective formulations of the charge generation layer and the charge transport layer are the same as previously described in FIG. 3.

The electrophotographic photoconductor shown in FIG. 5 can be obtained by forming the protective layer 6 on the charge generation layer 5 obtained in FIG. 4 by spray coating an appropriate resin solution. As a resin to be employed in the protective layer 6, any binder agents to be described later can be used.

Specific examples of materials for the electroconductive substrate 1 of the electrophotographic photoconductor according to the present invention include a metallic plate or foil made of aluminum, a plastic film on which a metal such as aluminum is deposited, and a sheet of paper which has been treated so as to be electroconductive.

Specific examples of the binder agent for use in the present invention are condensation resins such as polyamide, polyurethane, polyester, epoxy resin, polyketone and polycarbonate; and vinyl copolymers such as polyvinylketone, polystyrene, poly-N-vinylcarbazole and polyacrylamide. All the resins having insulating properties and adhesive properties can be employed.

Some plasticizers may be added to the above-mentioned binder agent, when necessary. Examples of such plasticizers are halogenated paraffin, polybiphenyl chloride, dimethylnaphthalene and dibutyl phthalate.

Furthermore, in the electrophotographic photoconductors according to the present invention,.an adhesive layer or a barrier layer can be interposed between the electroconductive substrate and the photoconductive layer when necessary. Examples of the material for use in the adhesive layer or the barrier layer are polyamide, nitrocellulose and aluminum oxide. It is preferable that the thickness of the adhesive layer or the barrier layer be 1 μm or less.

When copying is performed by use of the photoconductors according to the present invention, the surface of the photoconductor is charged uniformly in the dark to a predetermined polarity. The uniformly charged photoconductor is exposed to a light image so that a latent electrostatic image is formed on the photoconductor. The thus formed latent electrostatic image is developed by a developer to a visible image, and when necessary, the developed image can be transferred to a sheet of paper. The electrophotographic photoconductors according to the present invention have the advantages in that the photosensitivity is high and the flexibility is improved.

Other features of this invention will become apparent in the course of the following description of exemplary embodiments, which are given for illustration of the invention and are not intended to be limiting thereof.

SYNTHESIS EXAMPLE 1

[Synthesis of N-(4-methylphenyl)-N-(3-nitrophenyl)-1-pyrenylamine]

90 ml of nitrobenzene was added to a mixture of 10.04 g (44 mmol) of 4-methyl-3'-nitrodiphenylamine, 17.33 g (53 mmol) of 1-iodopyrene, 12.16 g of potassium carbonate, and 2.80 g of copper powder. The thus obtained mixture was subjected to azeotropic dehydration in a stream of nitrogen, using an ester tube, with stirring, at 210° C. for 7.5 hours.

After the mixture was cooled to room temperature, the above mixture was filtrated by use of a Celite. Nitrobenzene was removed from the thus obtained filtrate under reduced pressure.

The thus obtained residue was extracted with chloroform, washed with water, and dried over magnesium sulfate. This extract was concentrated under reduced pressure, so that an oily dark brown material was obtained.

This oily material was chromatographed on a silica gel column using as an eluting solution a mixed solvent of toluene and n-hexane at a ratio of 2:3 (vol). The thus obtained product was recrystallized from a mixed solvent of toluene and ethanol, whereby 11.47 g of N-(4-methylphenyl)-N-( 3-nitrophenyl)-1-pyrenylamine represented by formula (A) was obtained as orange yellow needle crystals in a 60.8% yield.

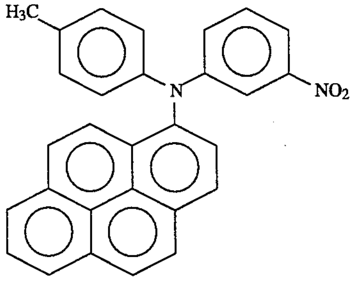
(A)

The melting point of the above compound was 180.0° to 182.0° C. The results of the elemental analysis of the compound were as follows:

| | % C | % H | % N |
|---|---|---|---|
| Calculated | 81.29 | 4.70 | 6.54 |
| Found | 81.56 | 4.50 | 6.38 |

The above calculation was based on the formula for N-(4-methylphenyl)-N-(3-nitrophenyl)-1-pyrenylamine of $C_{29}H_{20}N_2O_2$.

Figure 6:
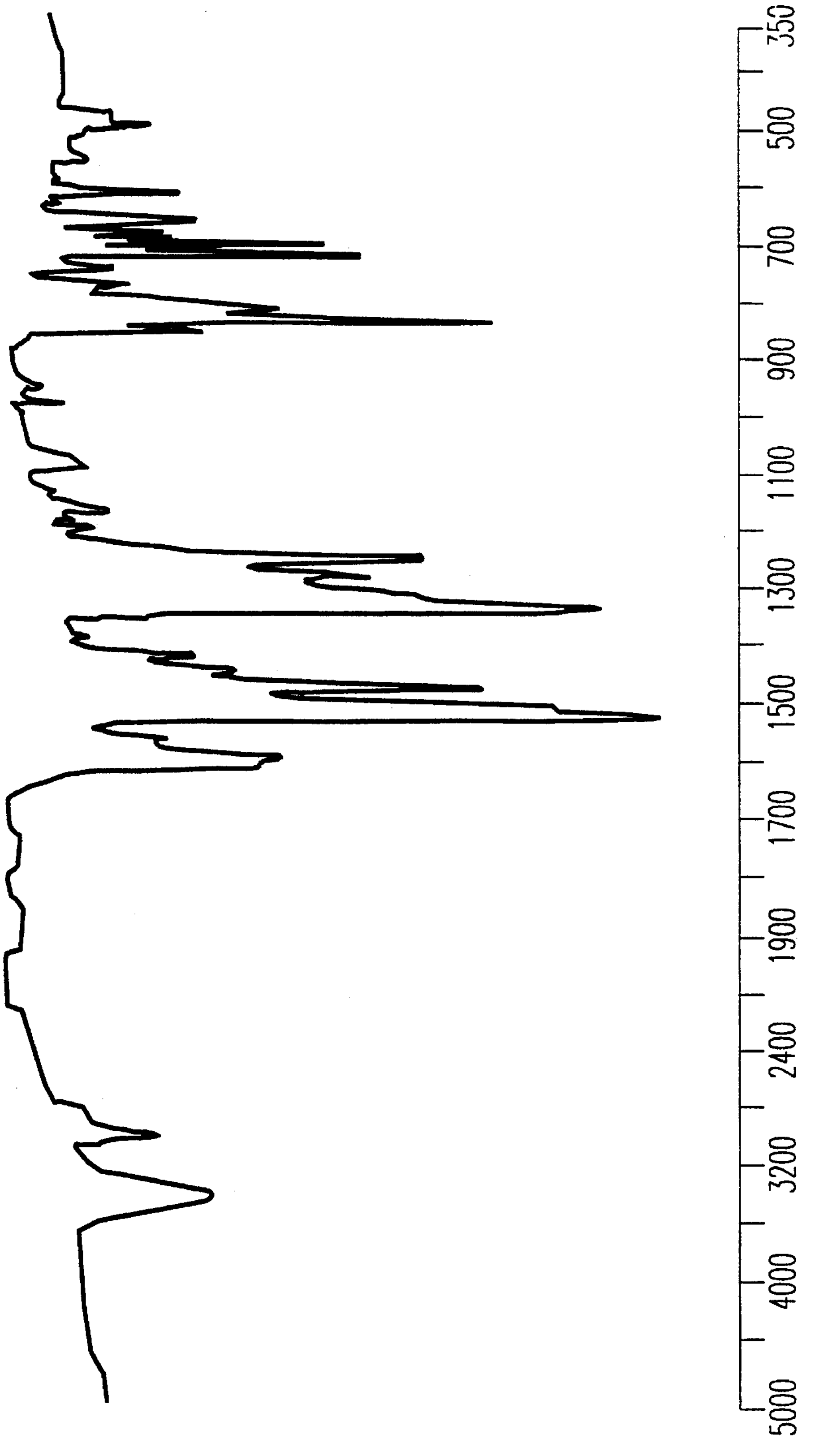
FIG. 6 is an IR spectrum of an N-phenyl-N-(3-nitrophenyl)- 1-pyrenylamine derivative obtained in Synthesis Example 1.

FIG. 6 shows an IR spectrum of the above compound taken by use of a KBr tablet.

SYNTHESIS EXAMPLE 2

[Synthesis of N-(4-methylphenyl)-N-(3-aminophenyl)-1-pyrenylamine]

12.11 g of N-(4-methylphenyl)-N-(3-nitrophenyl)-1-pyrenylamine synthesized in Synthesis Example 1 was dissolved in 120 ml of tetrahydrofuran. 1.21 g of a 5% palladium-carbon was added to the above obtained solution. The thus obtained mixture was placed in a shaking type hydrogenation apparatus and-hydrogenated at room temperature and 1 atmospheric pressure.

After the completion of the hydrogenation reaction, the obtained product was filtrated by use of a Celite. The thus obtained filtrate was concentrated under reduced pressure, so that an oily orange material was obtained. This material was refluxed with stirring together with n-hexane, whereby 10.82 g of N-(4-methylphenyl)-N-(3-aminophenyl)-1-pyrenylamine represented by formula (B) was obtained as a yellow powder in a 96.1% yield.

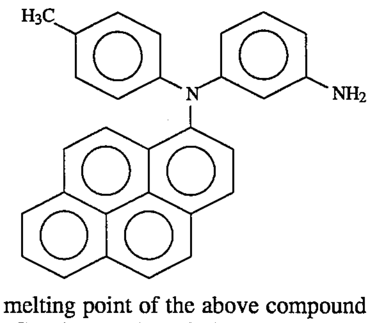
(B)

The melting point of the above compound was 153.0° to 158.0° C. The results of the elemental analysis of the compound were as follows:

| | % C | % H | % N |
|---|---|---|---|
| Calculated | 87.40 | 5.57 | 7.03 |
| Found | 87.71 | 5.27 | 6.81 |

The above calculation was based on the formula for N-(4-methylphenyl)-N-(3-aminophenyl)-1-pyrenylamine of $C_{29}H_{22}N_2$.

Figure 7:
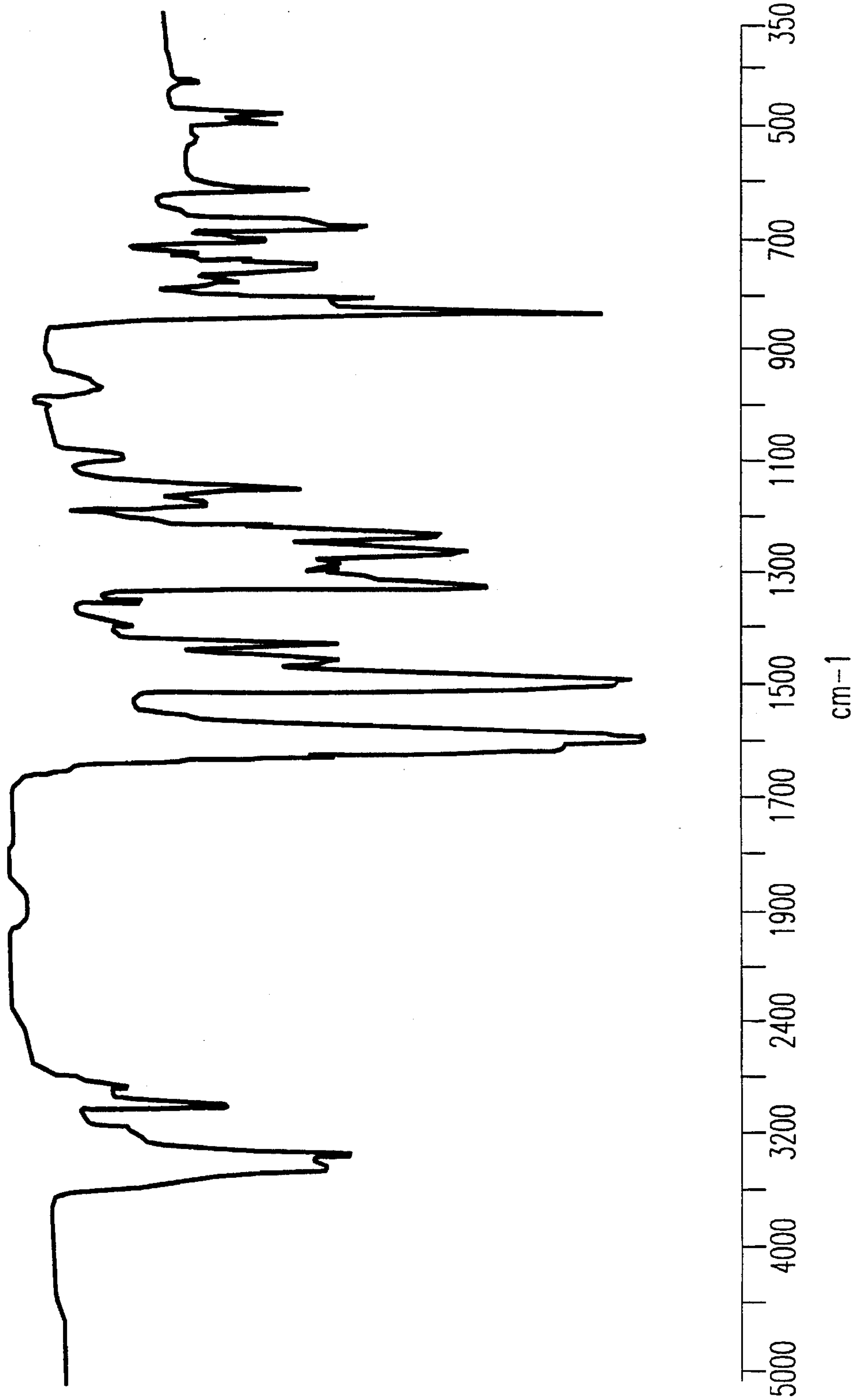
FIG. 7 is an IR spectrum of an N-phenyl-N-(3-aminophenyl)- 1-pyrenylamine derivative obtained in Synthesis Example 2.

FIG. 7 shows an IR spectrum of the above compound taken by use of a KBr tablet.

SYNTHESIS EXAMPLE 3-1

[Synthesis of N-(4-methylphenyl)-N-[3-bis(4-methylphenyl)aminophenyl]-1-pyrenylamine (Compound No. 12 in Table 1)]

A mixture of 2.79 g (7.00 mmol) of N-(4-methylphenyl)-N-( 3-aminophenyl)-1-pyrenylamine synthesized in Synthesis Example 2, 15.3 g (70.0 mmol) of 4-iodotoluene, 3.87 g of potassium carbonate, and 0.44 g of copper powder was subjected to azeotropic dehydration in a stream of nitrogen, using an ester tube, with stirring, at 209° to 212° C. for 10 hours.

After the mixture was cooled to room temperature, it was filtrated by use of a Celite. Chloroform was added to the thus obtained filtrate. The chloroform layer was separated and washed with water and dried over magnesium sulfate. The thus obtained extract was concentrated under reduced pressure, so that an oily dark brown material was obtained.

This oily material was chromatographed on a silica gel column using as an eluting solution a mixed solvent of toluene and n-hexane at a ratio of 1:3. The thus obtained product was recrystallized from a mixed solvent of 1,4-dioxane and ethanol, whereby 1.81 g of N-(4-methylphenyl)-N-[3-bis(4-methylphenyl)aminophenyl]-1-pyrenylamine represented by formula (C) was obtained as yellow needle crystals in a 44.7% yield.

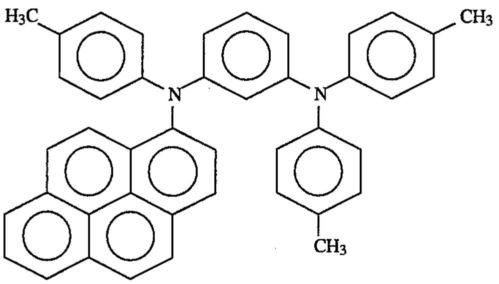
(C)

The melting point of the above compound was 190.0° to 191.0° C. The results of the elemental analysis of the compound were as follows:

| | % C | % H | % N |
|---|---|---|---|
| Calculated | 89.24 | 5.92 | 4.84 |
| Found | 89.17 | 5.74 | 4.76 |

The above calculation was based on the formula for N-(4-methylphenyl)-N-[3-bis(4-methylphenyl)aminophenyl] -1-pyrenylamine of $C_{43}H_{34}N_2$.

Figure 8:
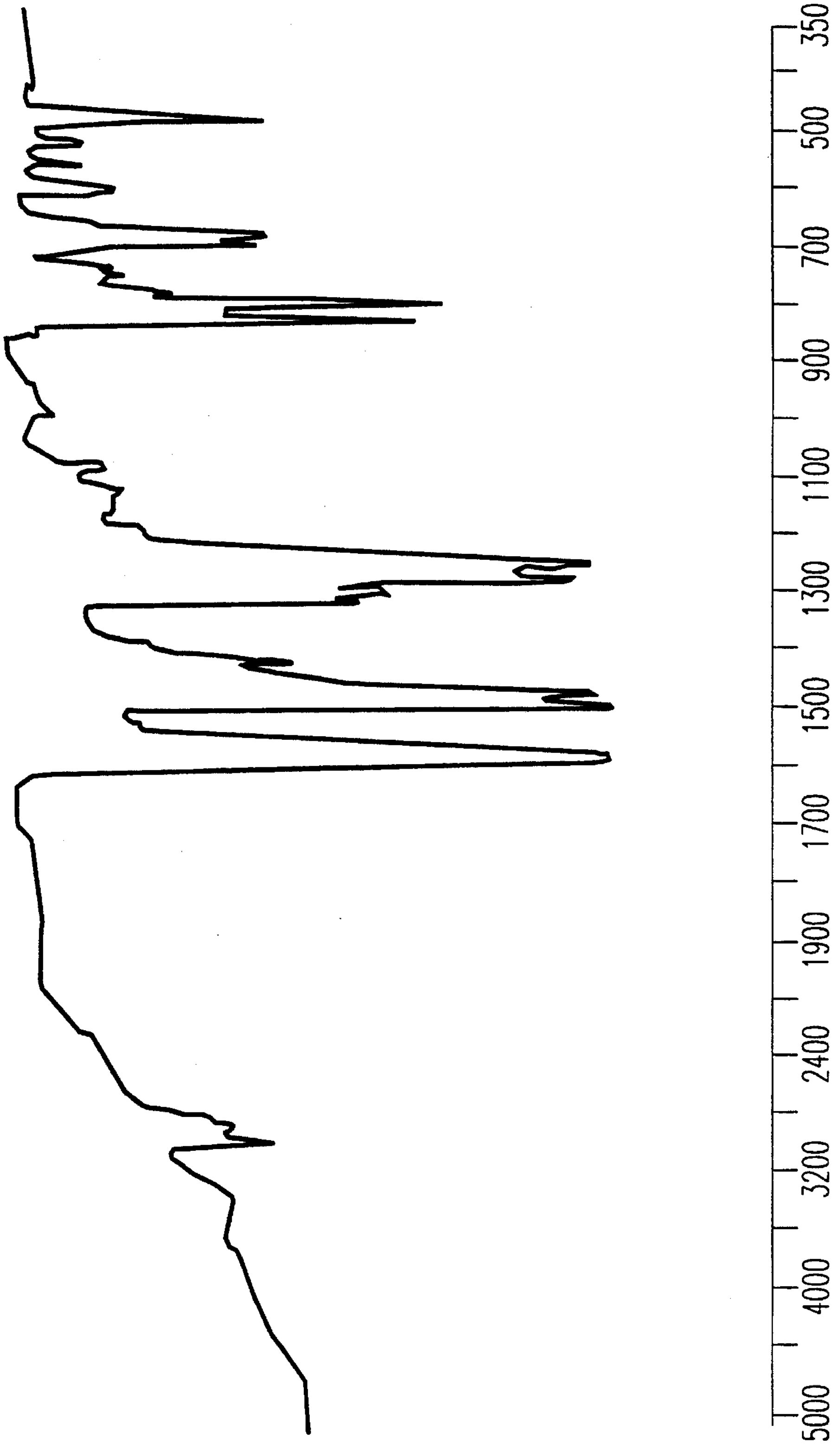
FIG. 8 is an IR spectrum of an N-phenyl-N-(3-diphenylaminophenyl)- 1-pyrenylamine derivative obtained in Synthesis Example 3-1.

FIG. 8 shows an IR spectrum of the above compound taken by use of a KBr tablet.

SYNTHESIS EXAMPLES 3-2 to 3-5

The procedure for preparing N-(4-methylphenyl)-N-[3 -bis(4-methylphenyl)aminophenyl]-1-pyrenylamine in Synthesis Example 3-1 was repeated except that N-(4-methylphenyl)-N-(3-aminophenyl)-1-pyrenylamine and 4-iodotoluene employed in Synthesis Example 3-1 were respectively replaced by each of N-phenyl-N-(3-aminophenyl)-1-pyrenylamine derivatives of formula (III) and halogenated benzene derivatives of formula (IV) having $R^8$ and $R^9$ shown in Table 2, whereby N-phenyl-N-(3-diphenylaminophenyl)-1-pyrenylamine derivatives shown in Table 2 were obtained. The melting points and the results of the elemental analysis of the above obtained compounds are also shown in Table 2.

TABLE 2

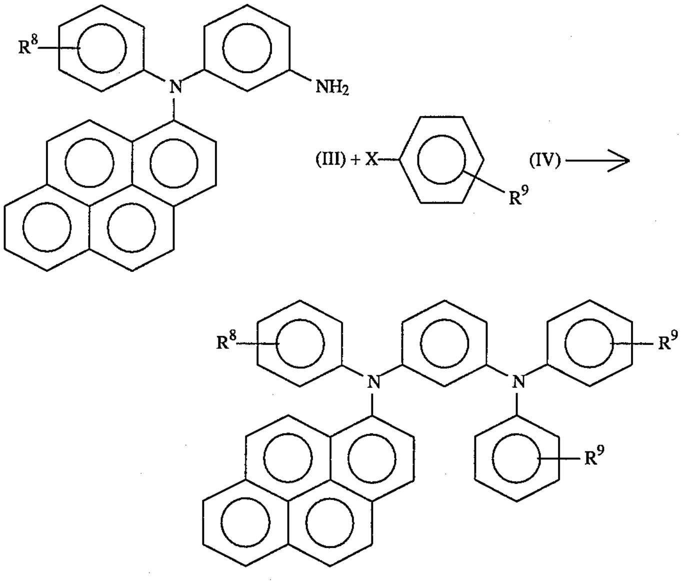
(II)

| Synthesis | Compound No. in | Melting Point | Elemental Analysis Found (Calculated) |
|---|---|---|---|

TABLE 2-continued

| Ex. No. | Table 1 | $R^8$ | $R^9$ | (°C.) | % C | % H | % N |
|---|---|---|---|---|---|---|---|
| Ex. 2 | 9 | 4-$CH_3$ | H | 147.5–150.5 | 89.38 (89.42) | 5.32 (5.49) | 4.97 (5.09) |
| Ex. 3 | 14 | 4-$CH_3$ | 4-$OCH_3$ | 144.0–152.0 | 84.44 (84.56) | 5.50 (5.61) | 4.60 (4.59) |
| Ex. 4 | 6 | H | 4-$CH_3$ | 195.5–196.5 | 89.17 (89.33) | 5.59 (5.71) | 4.81 (4.96) |
| Ex. 5 | 7 | H | 4-$OCH_3$ | 165.0–167.0 | 84.74 (84.53) | 5.12 (5.41) | 4.67 (4.70) |

EXAMPLE 1

76 parts by weight of Diane Blue (C.I. Pigment Blue 25: C.I. 21180) serving as a charge generating material, 1260 parts by weight of a 2% tetrahydrofuran solution of a polyester resin (Trademark "Vylon 200" made by Toyobo Company, Ltd.) and 3700 parts by weight of tetrahydrofuran were dispersed and ground in a ball mill. The thus prepared dispersion was coated on an aluminum surface of an aluminum-deposited polyester film serving as an electroconductive substrate by a doctor blade, and dried at room temperature, so that a charge generation layer with a thickness of about 1 μm was formed on the electroconductive substrate.

2 parts by weight of N-(4-methylphenyl)-N-[3-bis(4 -methylphenyl)aminophenyl]-1-pyrenylamine (Compound No. 12 in Table 1) prepared in Synthesis Example 3-1 serving as a charge transporting material, 2 parts by weight of polycarbonate resin (Trademark "Panlite K-1300" made by Teijin Limited.) and 16 parts by weight of tetrahydrofuran were mixed to prepare a coating liquid for a charge transport layer. This liquid was coated on the above formed charge generation layer by a doctor blade, and dried at 80° C. for 2 minutes and then at 120° C. for 5 minutes, so that a charge transport layer with a thickness of about 20 μm was formed on the charge generation layer. Thus an electrophotographic photoconductor No. 1 according to the present invention was prepared.

EXAMPLE 2 to 33

The procedure for preparing the electrophotographic photoconductor No. 1 in Example 1 was repeated except that Diane Blue serving as a charge generating material for use in the charge generation layer and the Compound No. 12 serving as a charge transporting material for use in the charge transport layer in Example 1 were respectively replaced by each of the charge generating materials and charge transporting materials listed in the following Table 3, whereby electrophotographic photoconductors No. 2 to No. 33 according to the present invention were prepared.

TABLE 3
| Photo-conductor | Charge Generating Material | Charge Transporting Material (m-phenylenediamine Derivative No.) |
| --- | --- | --- |
| 1 | 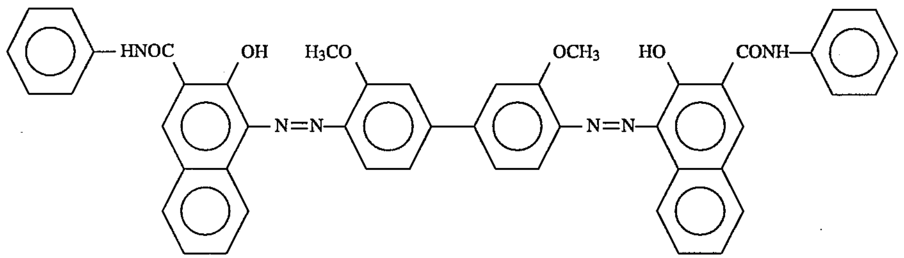 | 12 |
| 2 | 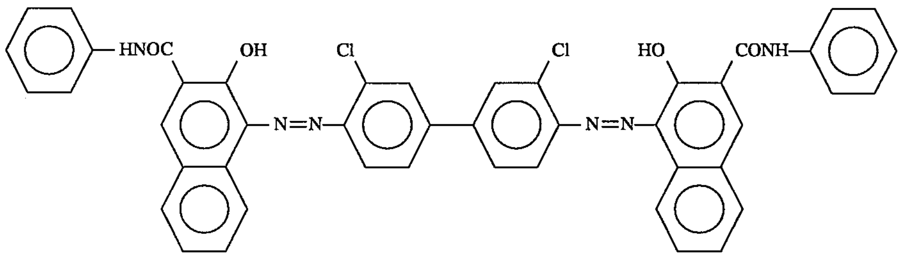 | 12 |
| 3 | 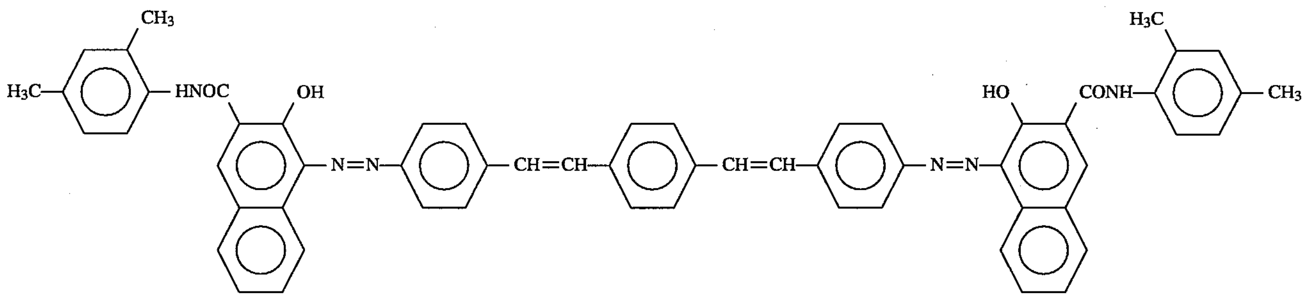 | 12 |

TABLE 3-continued
| Photo-conductor | Charge Generating Material | Charge Transporting Material (m-phenylenediamine Derivative No.) |
| --- | --- | --- |
| 4 | 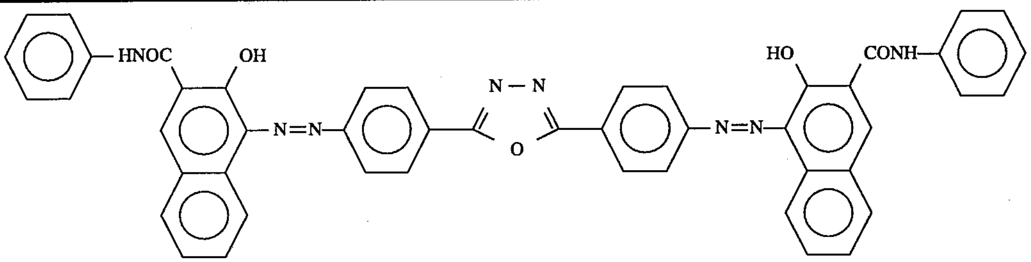 | 12 |
| 5 | 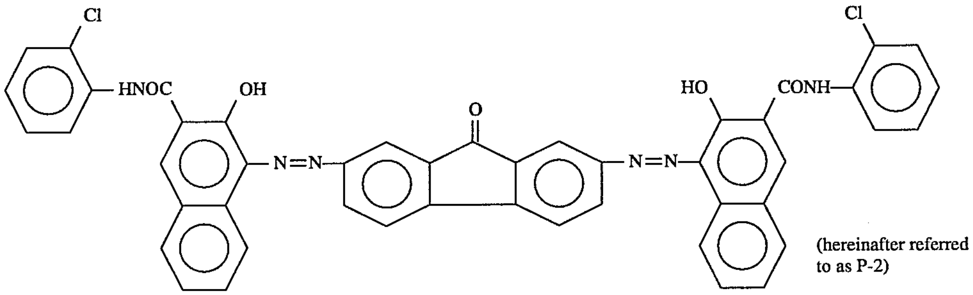 (hereinafter referred to as P-2) | 12 |

TABLE 3-continued
| Photo-conductor | Charge Generating Material | Charge Transporting Material (m-phenylenediamine Derivative No.) |
| --- | --- | --- |
| 6 | 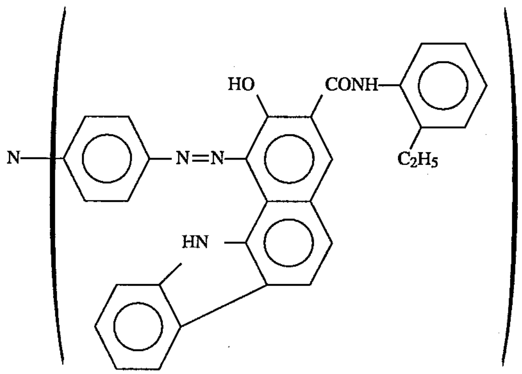 3 (hereinafter referred to as P-3) | 12 |
| 7 | β-type Copper Phthalocyanine | 12 |
| 8 | 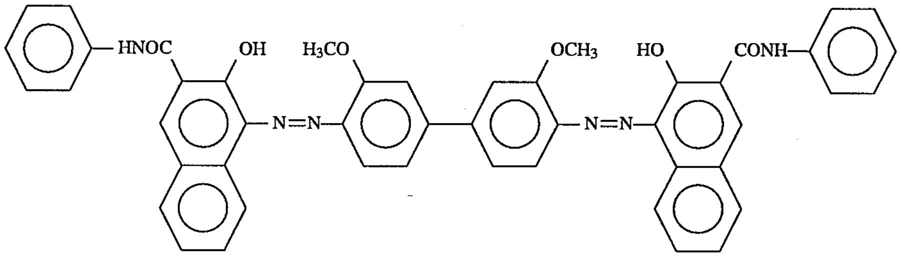 | 9 |

TABLE 3-continued
| Photo-conductor | Charge Generating Material | Charge Transporting Material (m-phenylenediamine Derivative No.) |
|---|---|---|
| 9 | 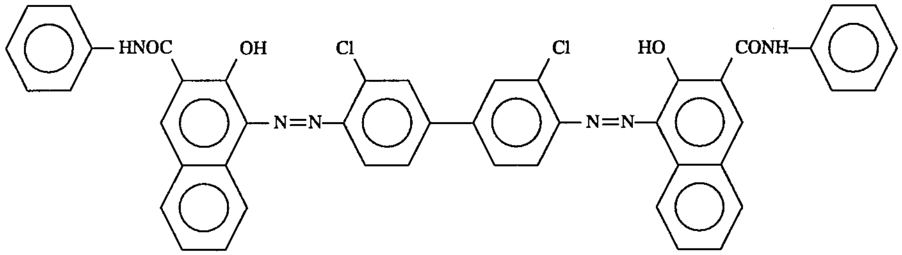 | 9 |
| 10 | P-1 | 9 |
| 11 | P-2 | 9 |
| 12 | P-3 | 9 |
| 13 | P-1 | 3 |
| 14 | P-2 | 3 |
| 15 | P-3 | 3 |
| 16 | P-1 | 14 |
| 17 | P-2 | 14 |
| 18 | P-3 | 14 |
| 19 | P-1 | 21 |
| 20 | P-2 | 21 |
| 21 | P-3 | 21 |
| 22 | P-1 | 25 |
| 23 | P-2 | 25 |
| 24 | P-3 | 25 |
| 25 | P-1 | 31 |
| 26 | P-2 | 31 |
| 27 | P-3 | 31 |
| 28 | P-1 | 34 |
| 29 | P-2 | 34 |
| 30 | P-3 | 34 |
| 31 | P-1 | 37 |
| 32 | P-2 | 37 |
| 33 | P-3 | 37 |

EXAMPLE 34

Selenium was vacuum-deposited on an aluminum plate with a thickness of about 300 μm, so that a charge generation layer with a thickness of about 1 μm was formed on the aluminum plate.

2 parts by weight of the Compound No. 12, 3 parts by weight of polyester resin (Trademark "Polyester Adhesive 49000" made by Du Pont de Nemours, E.I. & Co.) and 45 parts by weight of tetrahydrofuran were mixed to prepare a coating liquid for a charge transport layer. This liquid was coated on the above formed charge generation layer by a doctor blade, and dried at room temperature and then under reduced pressure, so that a charge transport layer with a thickness of about 10 μm was formed on the charge generation layer. Thus an electrophotographic photoconductor No. 34 according to the present invention was prepared.

EXAMPLE 35

The procedure for preparing the electrophotographic photoconductor No. 34 in Example 34 was repeated except that a charge generation layer with a thickness of about 0.6 μm was formed on the same aluminum plate as employed in Example 34 by deposition of the following perylene pigment instead of selenium, so that an electrophotographic photoconductor No. 35 according to the present invention was prepared:

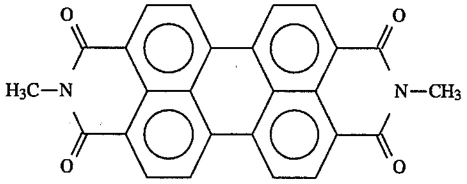

EXAMPLE 36

1 part by weight of the same Diane Blue as employed in Example 1 and 158 parts by weight of tetrahydrofuran were mixed and ground in a ball mill to prepare a dispersion. To the thus prepared dispersion, 12 parts by weight of the Compound No. 12 prepared in Synthesis Example 3-1 and 18 parts by weight of polyester resin (Trademark "Polyester Adhesive 49000" made by Du Pont de Nemours, E.I. & Co.) were added to prepare a coating liquid for a photoconductive layer. This liquid was coated on an aluminum-deposited polyester film serving as an electroconductive substrate by a doctor blade, and dried at 100° C. for 30 minutes, so that a photoconductive layer with a thickness of about 16 μm was formed on the electroconductive substrate. Thus, an electrophotographic photoconductor No. 36 according to the present invention was prepared.

EXAMPLE 37

2 parts by weight of the Compound No. 12 serving as a charge transporting material, 2 parts by weight of polycarbonate resin (Trademark "Panlite K-1300" made by Teijin Limited.) and 16 parts by weight of tetrahydrofuran were mixed to prepare a coating liquid for a charge transport layer. This liquid was coated on an aluminum-deposited polyester film serving as an electroconductive substrate by a doctor blade, and dried at 80° C. for 2 minutes and then at 120° C. for 5 minutes, so that a charge transport layer with a thickness of about 20 μm was formed on the electroconductive substrate.

13.5 parts by weight of bisazo pigment (P-2), 5.4 parts by weight of polyvinyl butyral (Trademark "XYHL" made by Union Carbide Japan K.K.), 680 parts by weight of tetrahydrofuran and 1020 parts by weight of ethyl cellosolve were mixed and ground in a ball mill to prepare a dispersion. To this dispersion, 1700 parts by weight of additional ethyl cellosolve were added and stirred to prepare a coating liquid for a charge generation layer. This liquid was coated on the above formed charge transport layer by spray coating and dried at 100° C. for 10 minutes, so that a charge generation layer with a thickness of about 0.2 μm was formed on the charge transport layer.

A methanol/n-butanol solution of a polyamide resin (Trademark "CM-8000" made by Toray Industries, Inc.) was coated on the above formed charge generation layer by spray coating and dried at 120° C. for 30 minutes, so that a protective layer with a thickness of about 0.5 μm was formed on the charge generation layer. Thus, an electrophotographic photoconductor No. 37 according to the present invention was prepared.

Each of the thus prepared electrophotographic photoconductors No. 1 to No. 37 according to the present invention was charged under application of −6 kV or +6 kV of corona charge for 20 seconds, using a commercially available electrostatic copying sheet testing apparatus ("Paper Analyzer Model SP-428" made by Kawaguchi Electro Works Co., Ltd.). Then, each electrophotographic photoconductor was allowed to stand in the dark for 20 seconds without applying any charge thereto, and the surface potential Vpo (V) of the photoconductor was measured. Each photoconductor was then illuminated by a tungsten lamp in such a manner that the illuminance on the illuminated surface of the photoconductor was 4.5 lux, and the exposure $E_{1/2}$ (lux.sec) required to reduce the initial surface potential Vpo (V) to ½ thereof was measured. The results are shown in Table 4.

Furthermore, each of the electrophotographic photoconductors No. 1 to No. 37 according to the present invention was charged by use of a commercially available electrophotographic copying machine. Then a latent electrostatic image was formed on the photoconductor using an original by illuminating the charged photoconductor. The thus formed latent electrostatic image was developed by a dry-type developer to a visible image. The thus obtained toner image was electrostatically transferred and fixed onto a sheet of normal paper, so that a clear transferred image was obtained. A clear image was also obtained when a wet-type developer was employed for development of the latent electrostatic image.

TABLE 4

| Photoconductor No. | Vpo (V) | $E_{1/2}$ (lux · sec) |
|---|---|---|
| 1 | −1352 | 1.05 |
| 2 | −1213 | 1.02 |
| 3 | −1311 | 0.90 |
| 4 | −1315 | 1.22 |
| 5 | −1193 | 0.92 |
| 6 | −1053 | 0.59 |
| 7 | −821 | 0.31 |
| 8 | −1015 | 1.02 |
| 9 | −1305 | 0.98 |
| 10 | −1148 | 0.86 |
| 11 | −1055 | 0.88 |
| 12 | −1047 | 0.69 |
| 13 | −1153 | 0.92 |
| 14 | −1028 | 0.95 |

TABLE 4-continued

| Photoconductor No. | Vpo (V) | $E_{1/2}$ (lux · sec) |
|---|---|---|
| 15 | −1081 | 0.72 |
| 16 | −1166 | 0.90 |
| 17 | −1144 | 0.97 |
| 18 | −857 | 0.51 |
| 19 | −1021 | 0.88 |
| 20 | −1013 | 0.82 |
| 21 | −827 | 0.41 |
| 22 | −1057 | 0.95 |
| 23 | −1013 | 0.98 |
| 24 | −988 | 0.70 |
| 25 | −1212 | 0.83 |
| 26 | −1195 | 0.85 |
| 27 | −1048 | 0.57 |
| 28 | −1314 | 1.05 |
| 29 | −1218 | 1.10 |
| 30 | −1111 | 0.95 |
| 31 | −1158 | 0.90 |
| 32 | −1065 | 0.92 |
| 33 | −1051 | 0.69 |
| 34 | −910 | 1.57 |
| 35 | −1025 | 1.46 |
| 36 | +956 | 1.25 |
| 37 | +1089 | 0.98 |

The electrophotographic photoconductors of the present invention exhibit an significantly improved resistance to heat and mechanical shocks as well as the photoconductive properties thereof. Furthermore, the photoconductors according to the present invention can be manufactured at low cost.

The novel N-phenyl-N-(3-diphenylaminophenyl)-1-pyrenylamine derivatives and N-phenyl-N-(3-aminophenyl)-1-pyrenylamine derivatives for use in the photoconductors of the present invention are remarkably effective as photoconductive materials in the electrophotographic photoconductors and are optically or chemically sensitized with a sensitizer such as a dye or a Lewis acid. Therefore, these derivatives are applicable to charge transporting materials contained in a photoconductive layer of the electrophotographic photoconductor, specifically of a function-separating type electrophotographic photoconductor comprising a charge generation layer and a charge transport layer. The novel N-phenyl-N-(3-nitrophenyl)-1-pyrenylamine derivatives of the present invention are usable as intermediates for synthesizing the above-mentioned N-phenyl-N-( 3-aminophenyl)-1-pyrenylamine derivatives.

What is claimed is:

1. An N-phenyl-N-(3-diphenylaminophenyl)- 1-pyrenylamine derivative of formula (II):

(II)

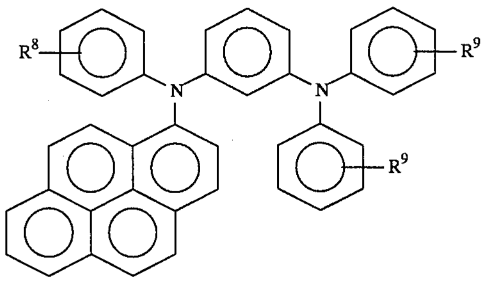

wherein $R^8$ and $R^9$ each represent hydrogen, an alkyl group having 1 to 12 carbon atoms which is optionally substituted by a substituent selected from the group consisting of a phenyl group, a halogen atom, an alkoxyl group and an aryloxy group, an alkoxyl group having 1 to 12 carbon atoms which is optionally substituted by a substituent selected from the group consisting of a phenyl group, a halogen atom, an alkoxyl group and an aryloxy group, or a phenyl group which is optionally substituted by a substituent selected from the group consisting of an alkyl group having 1 to 8 carbon atoms, an alkoxyl group having 1 to 8 carbon atoms and a halogen atom.

2. The N-phenyl-N-(3-diphenylaminophenyl)-1-pyrenylamine compound as claimed in claim 1, wherein said alkyl group represented by $R^8$ or $R^9$ has a substituent selected from the group consisting of a phenyl group, a halogen atom, an alkoxyl group and an aryloxy group.

3. The N-phenyl-N-(3-diphenylaminophenyl)-1-pyrenylamine compound as claimed in claim 1, wherein said alkoxyl group represented by $R^8$ or $R^9$ has a substituent selected from the group consisting of a phenyl group, a halogen atom, an alkoxyl group and an aryloxy group.

4. The N-phenyl-N-(3-diphenylaminophenyl)-1-pyrenylamine compound as claimed in claim 1, wherein said phenyl group represented by $R^8$ or $R^9$ has a substituent selected from the group consisting of an alkyl group having 1 to 8 carbon atoms, an alkoxyl group having 1 to 8 carbon atoms, and a halogen atom.

5. An N-phenyl-N-(3-aminophenyl)-1-pyrenylamine derivative of formula (III):

(III)

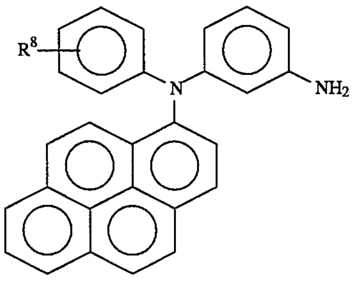

wherein $R^8$ represents hydrogen, an alkyl group having 1 to 12 carbon atoms which is optionally substituted by a substituent selected from the group consisting of a phenyl group, a halogen atom, an alkoxyl group and an aryloxy group, an alkoxyl group having 1 to 12 carbon atoms which is optionally substituted by a substituent selected from the group consisting of a phenyl group, a halogen atom, an alkoxyl group and an aryloxy group, or a phenyl group which is optionally substituted by a substituent selected from the group consisting of an alkyl group having 1 to 8 carbon atoms, an alkoxyl group having 1 to 8 carbon atoms and a halogen atom.

6. The N-phenyl-N-(3-aminophenyl)-1-pyrenylamine compound as claimed in claim 5, wherein said alkyl group represented by $R^8$ has a substituent selected from the group consisting of a phenyl group, a halogen atom, an alkoxyl group and an aryloxy group.

7. The N-phenyl-N-(3-aminophenyl)-1-pyrenylamine compound as claimed in claim 5, wherein said alkoxyl group represented by $R^8$ has a substituent selected from the group consisting of a phenyl group, a halogen atom, an alkoxyl group and an aryloxy group.

8. The N-phenyl-N-(3-aminophenyl)-1-pyrenylamine compound as claimed in claim 5, wherein said phenyl group represented by $R^8$ has a substituent selected from the group consisting of an alkyl group having 1 to 8 carbon atoms, an alkoxyl group having 1 to 8 carbon atoms, and a halogen atom.

9. An N-phenyl-N-(3-nitrophenyl)-1-pyrenylamine derivative of formula (VIII):

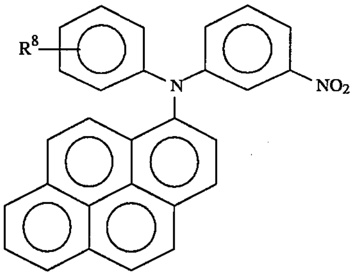

(VIII)

wherein $R^8$ represents hydrogen, an alkyl group having 1 to 12 carbon atoms which is optionally substituted by a substituent selected from the group consisting of a phenyl group, a halogen atom, an alkoxyl group and an aryloxy group, an alkoxyl group having 1 to 12 carbon atoms which is optionally substituted by a substituent selected from the group consisting of a phenyl group, a halogen atom, an alkoxyl group and an aryloxy group, or a phenyl group which is optionally substituted by a substituent selected from the group consisting of an alkyl group having 1 to 8 carbon atoms, an alkoxyl group having 1 to 8 carbon atoms and a halogen atom.

10. The N-phenyl-N-(3-nitrophenyl)-1-pyrenylamine compound as claimed in claim 9, wherein said alkyl group represented by $R^8$ has a substituent selected from the group consisting of a phenyl group, a halogen atom, an alkoxyl group and an aryloxy group.

11. The N-phenyl-N-(3-nitrophenyl)-1-pyrenylamine compound as claimed in claim 9, wherein said alkoxyl group represented by $R^8$ has a substituent selected from the group consisting of a phenyl group, a halogen atom, an alkoxyl group and an aryloxy group.

12. The N-phenyl-N-(3-nitrophenyl)-1-pyrenylamine compound as claimed in claim 9, wherein said phenyl group represented by $R^8$ has a substituent selected from the group consisting of an alkyl group having 1 to 8 carbon atoms, an alkoxyl group having 1 to 8 carbon atoms, and a halogen atom.

* * * * *

UNITED STATES PATENT AND TRADEMARK OFFICE
CERTIFICATE OF CORRECTION

PATENT NO. : 5,475,137

DATED : December 12, 1995

INVENTOR(S) : Tomoyuki SHIMADA et al

It is certified that error appears in the above-identified patent and that said Letters Patent is hereby corrected as shown below:

Column 6, line 43, "group-selected from" should read --group selected from--.

Column 16, line 31, "can be carried but" should read --can be carried out--.

Column 20, line 16, "layer a can be used" should read --layer 2a can be used--.

Column 21, line 2, "invention,.an adhesive," should read --invention, an adhesive--."

Signed and Sealed this

Thirteenth Day of August, 1996

Attest:

BRUCE LEHMAN

*Attesting Officer*

*Commissioner of Patents and Trademarks*